United States Patent
Jones et al.

(10) Patent No.: US 6,391,397 B1
(45) Date of Patent: May 21, 2002

(54) HIGH TRANSVERSE DIPOLE MOMENT ARYL COMPOUNDS

(75) Inventors: John Clifford Jones; Ian Charles Sage, both of Worcestershire; John William Goodby, E. Yorks; Michael Hird, E. Yorks; Robert Andrew Lewis, E. Yorks; Kenneth Johnson Toyne, E. Yorks, all of (GB)

(73) Assignees: Sharp Kabushiki Kaisha, Osaka (JP); The Secretary of State for Defence in Her Britannic Majesty's Government of the United Kingdom of Great Britain and Northern Ireland, Hampshire (GB)

( * ) Notice: Subject to any disclaimer, the term of this patent is extended or adjusted under 35 U.S.C. 154(b) by 0 days.

(21) Appl. No.: 09/543,058

(22) Filed: Apr. 5, 2000

(30) Foreign Application Priority Data

Apr. 14, 1999 (GB) .............................................. 9908361

(51) Int. Cl.[7] .......................... C09K 19/12; C07C 25/13

(52) U.S. Cl. ................... 428/1.1; 252/299.66; 570/127; 570/129; 570/131

(58) Field of Search ..................... 252/299.66, 299.61; 570/127, 129, 131; 428/1.1

(56) References Cited

FOREIGN PATENT DOCUMENTS

DE          4434976        *   4/1996

* cited by examiner

*Primary Examiner*—Shean C. Wu
(74) *Attorney, Agent, or Firm*—Renner, Otto, Boisselle & Sklar, LLP

(57) ABSTRACT

A fluorinated phenyl compound having the general formula [1]:

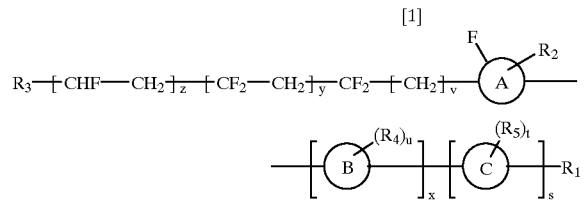

wherein each of s, v and x=0 or 1, each of t and u=1, 2 or 3, and each of y and z=0, 1 or 2; A, B and C are independently selected from conjugated cyclic moieties including heterorings and fused rings; $R_1$ and $R_3$ may be independently cyano, or $(C_1-C_{12})$alkyl, $(C_1-C_{12})$alkoxy, $(C_1-C_{11})$alkoxycarbonyl or $(C_1-C_{11})$alkylcarbonyloxy which may be fluoro- and/or cyano-substituted; $R_2$=H or F; $R_4$=H or F; and $R_5$=H or F. Such compounds have high transverse dipole moments and are potentially useful in liquid crystal compositions and in devices including same.

9 Claims, 1 Drawing Sheet

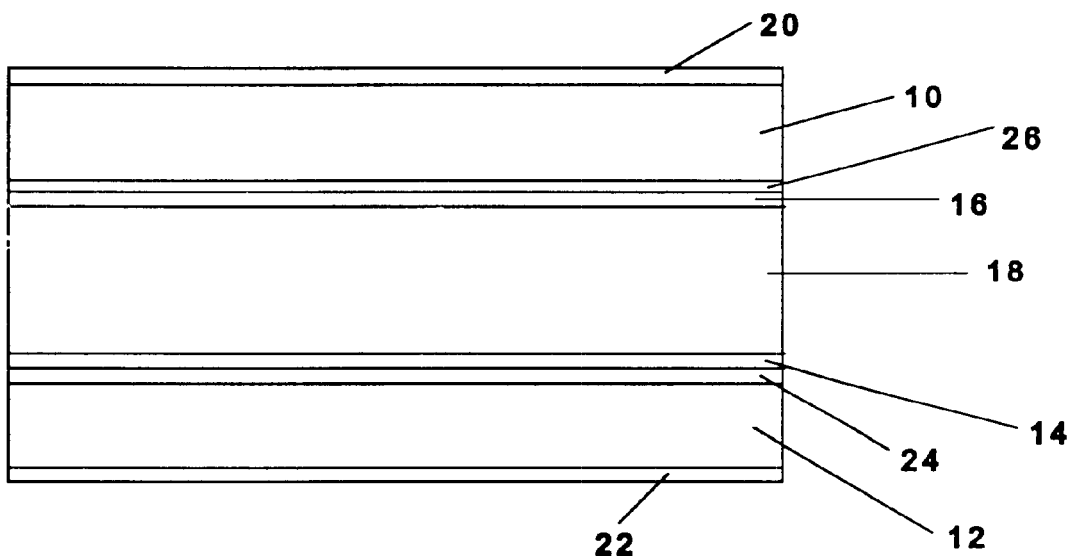
Fig.

HIGH TRANSVERSE DIPOLE MOMENT ARYL COMPOUNDS

BACKGROUND TO THE INVENTION

This invention relates to high transverse dipole moment aryl compounds and their use in liquid crystal compositions and liquid crystal devices wherein a high transverse dipole moment is required.

U.S. Pat. No. 4,784,793 discloses terpenoid derivatives for incorporation into ferroelectric liquid crystal mixtures, such terpenoid derivatives including aromatic esters of terpenoid alcohols in which the aromatic group includes two or three phenyl groups which may be biphenyl or terphenyl groups. The possibility of providing lateral substituents on one or more of these phenyl groups is disclosed with the object of fixing the orientation of such groups to add to the total lateral dipole moment of the molecule. The use of methyl, methoxy, trifluoromethyl, cyano, halogeno and acetyl groups as such lateral substituents is mentioned. U.S. Pat. No. 4,952,337 discloses similar types of compound to those disclosed in above-mentioned U.S. Pat. No. 4,784,793.

U.S. Pat. No. 4,852,977 discloses compounds which may be used as a host or dopant in ferroelectric chiral smectic liquid crystal mixtures, the compounds being derivatives of an α-hydroxycarboxylic acid containing a chiral unit in which the asymmetric carbon atom is linked to a hydrogen atom, a phenyl or phenyl alkyl group where the phenyl ring may be substituted with one or more alkyl, alkoxy, halogen or cyano groups, and two other moieties linked to the asymmetric carbon atom by carbonyloxy groups. The compound may include bi- or ter-phenyl groups which may or may not be substituted by one or more fluorine atoms to assist in sterically hindering rotation of the chiral centre relative to the core of the molecule.

It is an object of the present invention to provide a compound having an improved transverse dipole moment.

SUMMARY OF THE INVENTION

According to a first aspect of the present invention, there is provided a fluorinated aryl compound having the general formula [1]:

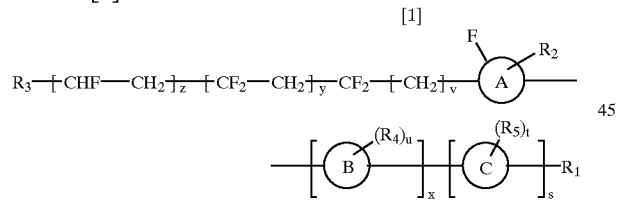

wherein
A, B and C are independently selected from conjugated cyclic moieties including heterorings and fused rings;
the fluoro substituent on ring A is at the ortho position relative to the attached end chain;
$R_1$=straight or branched, fluoro- and/or cyano-substituted or unsubstituted $(C_1-C_{12})$alkyl, straight or branched, fluoro- and/or cyano-substituted or unsubstituted $(C_1-C_{12})$alkoxy, straight or branched, fluoro- and/or cyano-substituted or unsubstituted $(C_1-C_{11})$ alkoxycarbonyl, straight or branched, fluoro- and/or cyano-substituted or unsubstituted $(C_1-C_{11})$ alkylcarbonyloxy, cyano, straight or branched, fluoro- and/or cyano-substituted or unsubstituted $(C_2-C_{12})$ alkenyl, straight or branched, fluoro- and/or cyano-substituted or unsubstituted $(C_2-C_{12})$alkenyloxy, straight or branched, fluoro- and/or cyano-substituted or unsubstituted $(C_2-C_{11})$alkenyloxycarbonyl, straight or branched, fluoro- and/or cyano-substituted or unsubstituted $(C_2-C_{11})$alkenylcarbonyloxy, or $R_6$—(CHF—$CH_2)_a$—$(CF_2$—$CH_2)_b$—$CF_2$—$(CH_2)_c$—;

$R_2$=H or F;

$R_3$=straight or branched, fluoro- and/or cyano-substituted or unsubstituted $(C_1-C_{12})$alkyl, straight or branched, fluoro- and/or cyano-substituted or unsubstituted $(C_1-C_{12})$alkoxy, straight or branched, fluoro- and/or cyano-substituted or unsubstituted $(C_1-C_{11})$ alkoxycarbonyl, straight or branched, fluoro- and/or cyano-substituted or unsubstituted $(C_1-C_{11})$ alkylcarbonyloxy, cyano, straight or branched, fluoro- and/or cyano-substituted or unsubstituted $(C_2-C_{12})$ alkenyl, straight or branched, fluoro- and/or cyano-substituted or unsubstituted $(C_2-C_{12})$alkenyloxy, straight or branched, fluoro- and/or cyano-substituted or unsubstituted $(C_2-C_{11})$alkenyloxycarbonyl, straight or branched, fluoro- and/or cyano-substituted or unsubstituted $(C_2-C_{11})$alkenylcarbonyloxy;

$R_4$=H or F;

$R_5$=H or F;

$R_6$=straight or branched, fluoro- and/or cyano-substituted or unsubstituted $(C_1-C_{12})$alkyl, straight or branched, fluoro- and/or cyano-substituted or unsubstituted $(C_1-C_{12})$alkoxy, straight or branched, fluoro- and/or cyano-substituted or unsubstituted $(C_1-C_{11})$ alkoxycarbonyl, straight or branched, fluoro- and/or cyano-substituted or unsubstituted $(C_1-C_{11})$ alkylcarbonyloxy, cyano, straight or branched, fluoro- and/or cyano-substituted or unsubstituted $(C_2-C_{12})$ alkenyl, straight or branched, fluoro- and/or cyano-substituted or unsubstituted $(C_2-C_{12})$alkenyloxy, straight or branched, fluoro- and/or cyano-substituted or unsubstituted $(C_2-C_{11}i)$alkenyloxycarbonyl, straight or branched, fluoro- and/or cyano-substituted or unsubstituted $(C_2-C_{11})$alkenylcarbonyloxy;

a=0, 1 or 2;
b=0, 1 or 2;
c=0 or 1;
s=0 or 1;
t=1, 2 or 3;
u=1, 2 or 3;
v=0 or 1;
x=0 or 1;
y=0, 1 or 2; and
z=0, 1 or 2;

More specifically, the compound of a fluorinated aryl compound may have the general formula [1a]:

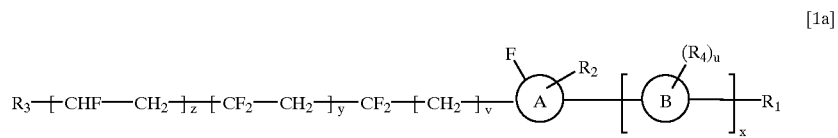

wherein u=1, 2 or 3, v=0 or 1, x=0, 1 or 2; y=0, 1 or 2; z=0, 1 or 2; A and B are independently selected from conjugated cyclic moieties including heterorings and fused rings; the fluoro substituent on ring A is at the ortho position relative to the chain containing $R_3$; $R_1$=$(C_1–C_{12})$alkyl, $(C_1–C_{12})$alkoxy, $(C_1–C_{11})$alkoxycarbonyl, $(C_1–C_{11})$alkylcarbonyloxy, or cyano; $R_2$=H or F, $R_3$=$(C_1–C_{11})$alkyl, $(C_1–C_{11})$alkoxy, $(C_1–C_{10})$alkoxycarbonyl or $(C_1–C_{10})$alkyl carbonyloxy; and $R_4$=H or F.

A, B and C are preferably aryl moieties, and are more preferably independently selected from phenyl, pyridinyl and pyrimidinyl.

Examples of compounds within the scope of the present invention are in accordance with the general formulae [2] to [12] below, wherein R is $(C_1–C_{10})$alkyl and R' is $(C_1–C_{12})$alkyl:

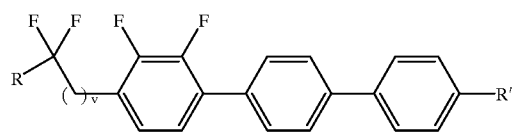

[2]

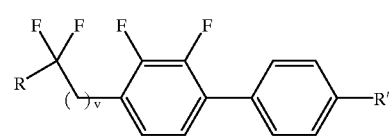

[3]

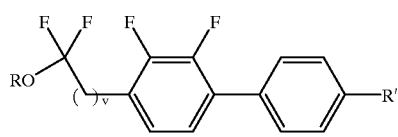

[4]

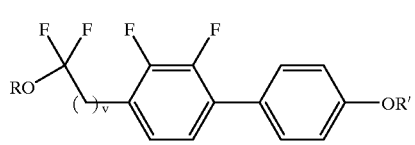

[5]

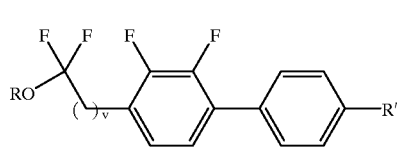

[6]

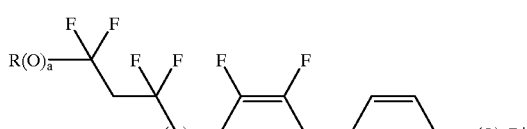

[7]

wherein a is 0 or 1, b is 0 or 1 and v is 0 or 1

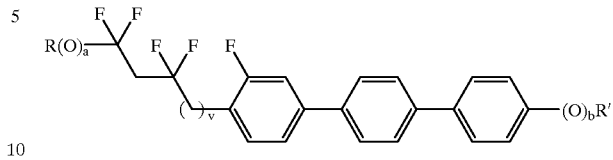

[7a]

wherein a is 0 or 1, b is 0 or 1 and v is 0 or 1

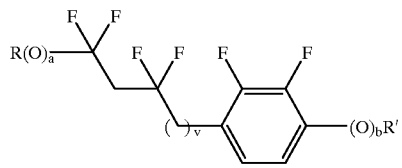

[8]

wherein a is 0 or 1, b is 0 or 1 and v is 0 or 1

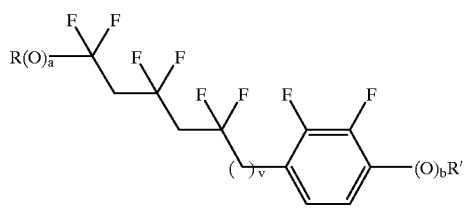

[9]

wherein a is 0 or 1, b is 0 or 1 and v is 0 or 1

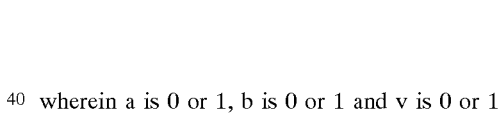

[10]

wherein a is 0 or 1, b is 0 or 1 and v is 0 or 1

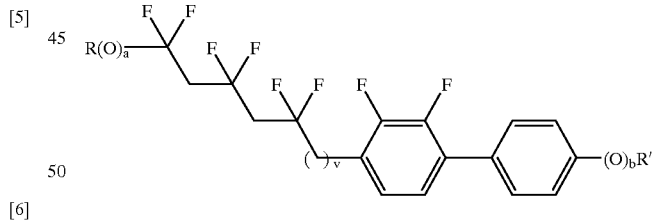

[11]

where a is 0 or 1, v is 0 or 1 and $R_2$ and $R_4$ are as defined above

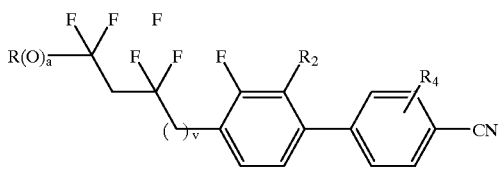

where a is 0 or 1, v is 0 or 1 and $R_2$ and $R_4$ are as defined above

In all of the above examples v=0 or 1, but in the case of terphenyl compounds, those compounds where v=0, i.e. where the side chain $CF_2$ group is at the alpha position relative to the adjacent ring, may be preferred.

Compounds of the general formulae [11] and [12] above are examples of nematics having a high positive dielectric biaxiality, i.e. nematics in which the liquid crystal molecules align parallel to the direction of an applied electrical field.

Compounds within the scope of the present invention also include compounds of the general formula:

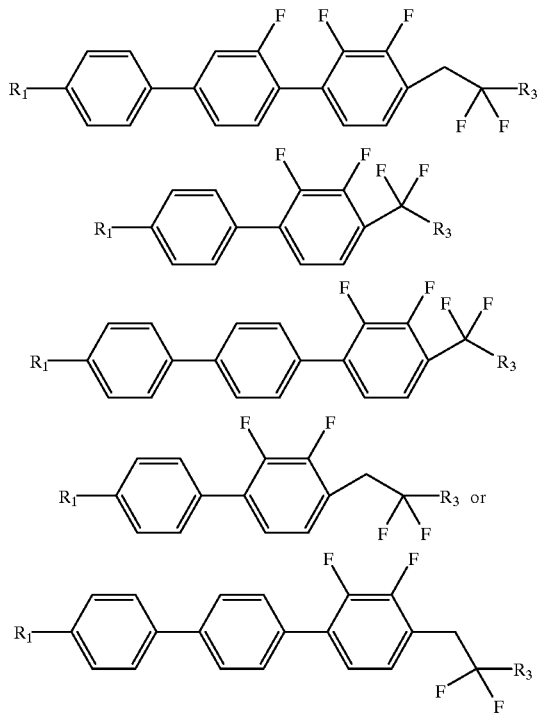

where $R_1$ is $(C_1-C_{12})$alkyl or $(C_1-C_{12})$alkoxy and $R_3$ is $(C_1-C_{12})$alkyl A particular example of a compound of the general formula [1] above is the compound having the formula [13] below:

[13]

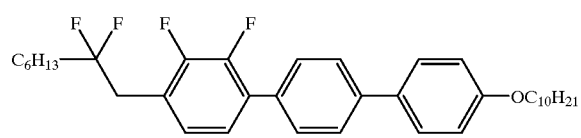

The measured dipole moment (following the procedure of E. P. Raynes (1984) Mol. Cryst. Liq. Cryst. Lett., v1 p 69) of compound [13] is $16.48 \times 10^{-30}$ Cm. Based on dipole moment calculations for a compound containing the moieties, R'O-phenyl-phenyl-3,4-difluorophenyl- and $RCF_2CH_2$—, the measured dipole moment for compound [13] is closest to the value predicted for a substantially parallel arrangement of the dipoles of these two moieties rather than an anti-parallel or random orientation. The estimated change of the nematic $\Delta\epsilon$ and SmC(*) $\delta\perp \approx \mu_\perp^2$, where $\epsilon_\perp$ is the dipole moment perpendicular to the long axis of the molecule. Since the measured dipole moment of a similar compound having no $RCF_2CH_2$— moiety was $10.9 \times 10^{-30}$ Cm, the compound [13] may represent an improvement of a factor of greater than 2 over the latter compound.

It is also considered that any tendency for the $CF_2$ fluorines to align parallel with the fluorine on the adjacent phenyl group of the core may enable suitable liquid crystal phases to be achieved with compounds having shorter cores than has heretofore been considered possible.

The difluoro side chain moiety in the compounds according to the present invention can be introduced using the following reaction scheme which is given, purely by way of example, in connection with a compound of the formula (1) wherein z and y are both 0.

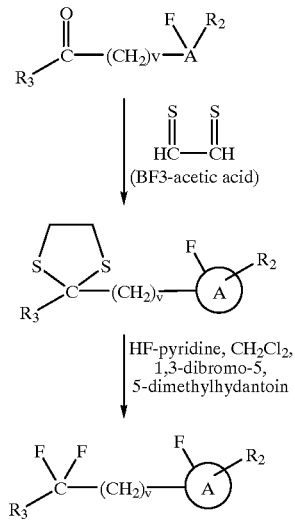

According to a second aspect of the present invention, there is provided a liquid crystal composition containing a compound according to said first aspect of the present invention.

The nature of compound of the invention chosen for use in the liquid crystal composition depends upon the nature of the device in which the composition is to be used, as will be apparent hereinafter.

According to a third aspect of the present invention, there is provided an electro-optical liquid crystal device including a liquid crystal cell have a layer of a liquid crystal composition according to said second aspect of the present invention, and means for applying an electrical field across said layer.

The present invention is particularly applicable to devices having any of the following:

(a) a nematic liquid crystal layer arranged to work in ECB or VAN mode, in which a large negative dielectric anisotropy $\Delta\epsilon$ is required for low voltage switching of the liquid crystal molecules into the plane of the cell, (b) a ferroelectric liquid crystal (FLC) layer using AC field stabilisation and/or τVmin (or reverse mode)

operation, in which a large positive dielectric anisotropy is required, (c) highly multiplexed nematic layers having SmC components with high negative dielectric anisotropy and/or high positive dielectric biaxiality for a steep electro-optical response and therefore a high level of multiplexibility, and (d) a nematic liquid crystal layer arranged to exhibit a large flexoelectric effect.

The present invention is also applicable to other devices, e.g. those containing antiferroelectric smectic materials or N* materials.

EXAMPLES IN ACCORDANCE WITH THE INVENTION

Example 1

The compound of the formula [13], namely

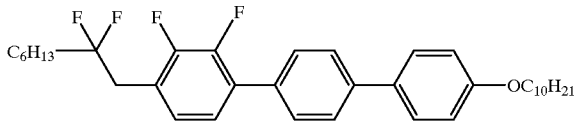

[13]

was prepared according to the following reaction scheme:

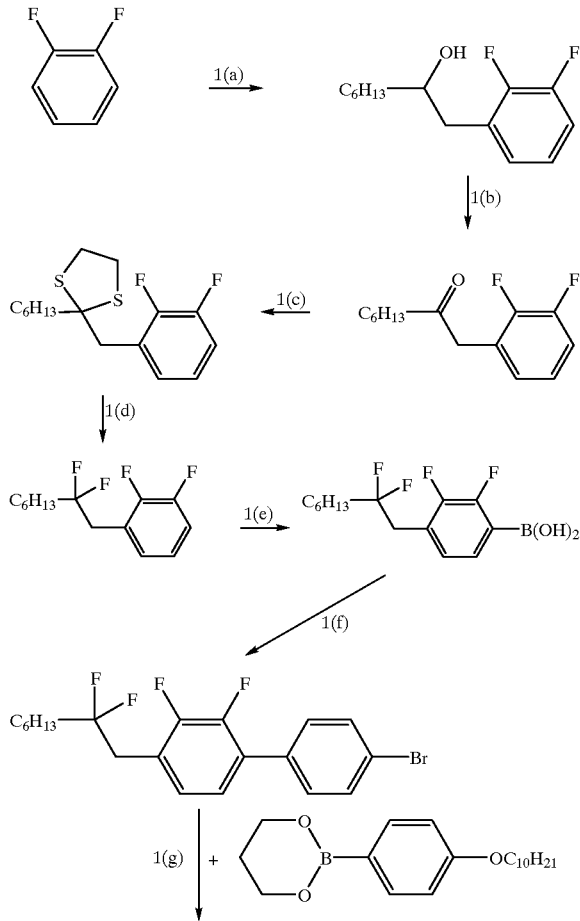

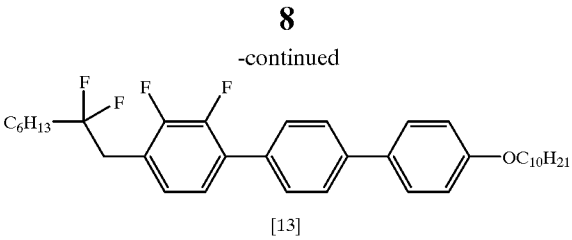

[13]

Reagents a . . . (i) n-butyllithium, −70° C., THF; (ii) 1,2-epoxyoctane; (iii) boron trifluoride etherate b . . . chromic acid, ether c . . . 1,2-ethanedithiol, boron trifluoride-acetic acid d . . . 70% hydrogen fluoride-pyridine, dichloromethane, 1,3-dibromo-5,5-dimethylhydantoin e . . . (i) n-butyllithium, −70° C., THF; (ii) trimethyl borate; (iii) 10% $HCl_{aq}$ f . . . 1-bromo-4-iodobenzene, 1,2-dimethoxyethane, 2 M $Na_2CO_3$, $Pd(PPh_3)_4$ g . . . 1,2-dimethoxyethane, 2 M $Na_2CO_3$, $Pd(PPh_3)_4$ Experimental Melting points and liquid crystal transition temperatures were measured using a Mettler FP5 hot-stage and control unit in conjunction with an Olympus BH2 polarising microscope. These were confirmed by differential scanning calorimetry (DSC) carried out on a Perkin Elmer DSC 7 with TAC 7/PC instrument interface and controlled cooling accessory. Heating and cooling rates were at 10° C. $min^{-1}$. A nitrogen atmosphere was maintained in the furnace. The reference sample was gold and the calibration sample was indium. Melting points for liquid crystalline compounds are those of the DSC onset value ($1^{st}$ heating cycle). Analytical thin-layer chromatography (TLC) was performed on Kieselgel silica 60 F254, backed onto aluminium sheets, and spots were visualised with UV light and iodine. The progress of reactions was often monitored using a Chrompak 9001 capillary gas chromatograph fitted with a CP-SIL 5 CB 10 m×0.25 mm, 0.12 μm column (Cat. No. 7700) ($N_2$ carrier) and a flame ionisation detector. Purity of compounds was checked by high performance liquid chromatography (HPLC) on a Lichrocart 125-4 Superspher RP18 column connected to a Merck-Hitachi L-4000 UV detector, L 6200A pump, D-6000 interface and D-6000 HPLC manager eluting with chloroform/acetonitrile. Infrared (IR) spectra were obtained using a Perkin Elmer 983G spectrometer (s=strong, w=weak) as thin films or potassium bromide discs. $^1H$ NMR spectra were recorded on a JEOL JMN GX270 FT spectrometer (270 MHz) or a JEOL 400 MHz machine in deuteriochloroform. Chemical shifts are reported in ppm from an internal standard of TMS. Selected data are reported as follows: chemical shift, multiplicity (s=singlet, d=doublet, t=triplet, q=quartet, m=multiplet, br=broad), coupling constant (hertz) and assignment. Mass spectra were recorded on a Finnigan MAT 1020 GC/MS spectrometer, $M^+$ represents the molecular ion. Flash chromatography was carried out using Sorbsil C60 (40–60 μm) grade silica. THF was freshly distilled from potassium. Light petroleum refers to the fraction (b.p. 40–60° C.) unless otherwise stated. Organic solvent extractions were dried over magnesium sulphate unless otherwise stated.

Step 1(a)—Preparation of 1-(2,3-Difluorophenyl)-octan-2-ol

To a stirred solution of 1,2-difluorobenzene 1 (20.0 g, 0.175 mol) in dry THF (300 ml) was added dropwise a solution of 2.5 M n-butyllithium (68 ml, 0.17 mol) at −70° C. under dry nitrogen. The addition rate was such that the temperature did not rise above −60° C. After the addition was completed the reaction was stirred at −70° C. for 2 h. 1,2-Epoxyoctane (21.6 g, 0.169 mol) was added slowly followed by the dropwise addition of boron trifluoride etherate (21 ml, 0.17 mol). The mixture was allowed to warm to room temperature overnight, acidified with 10% hydrochloric acid and extracted into ether. The combined extracts were washed with sat. aqueous sodium chloride and evaporated to give a viscous liquid. Kugelrohr distillation (130° C., 0.15 mm Hg) yielded 1-(2,3-difluorophenyl)-octan-2-ol (30.8 g, 74%) which crystallised on standing; $V_{max}$ 3370 br (OH), 2950, 2920, 2850, 1620, 1590, 1480 s, 1280, 1205, 1070 br, 825, 775, and 730 cm$^{-1}$, $\delta_H$ 0.88 (3 H, t, Me), 1.23–1.40 (10H, m, CH$_2$), 1.40–1.58 (4 H, m overlapping br s, CH$_2$CHOH and OH), 2.72 (1 H, ddd, J16, 8 and 2 Hz, ArCH$_2$), 2.91 (1 H, ddd, J16, 6, and 2 Hz, ArCH$_2$), 3.86 (1 H, m, CHOH), and 6.94–7.09 (3 H, m, ArH); m/z 242 (M$^+$), 225, 198, 157, 139, 128, and 97.

Step 1(b)—Preparation of 1-(2,3-Difluorophenyl)-octan-2-one

A solution of chromic acid[1] (31.6 ml, 21.0 mmol) was added dropwise to a rapidly stirred solution of the octan-2-ol produced in step 1(a) in ether (100 ml) cooled in a water bath. The mixture was stirred for 2 h; water was added and the mixture was extracted with ether (twice). The combined extracts were washed with water, 1 M aqueous sodium hydroxide, sat. sodium bicarbonate solution and dried and evaporated. Kugelrohr distillation (125° C., 0.02 mm Hg) gave the required ketone as a clear liquid (11.9 g, 80%); $v_{max}$ 2950, 2920, 2850, 1710 s (CO), 1620, 1590, 1480 s, 1410, 1275, 1205, 1060, 820, and 775 cm$^{-1}$, $\delta_H$ 0.90 (3 H, t, Me), 1.14–1.37 (6 H, m, CH$_2$), 1.60 (2 H, quint CH$_2$CH$_2$CO), 2.51 (2 H, t, CH$_2$CH$_2$CO), 3.75 (2 H, s, ArCH$_2$), and 6.87–7.13 (3 H, m, ArH); m/z 240 (M$^+$), 183, 171, 151, 141, 133, 127, and 113.

[1] B. S. Furniss, A. J. Hannaford, V. Rogers, P. W. G. Smith and A. R. Tatchell in Vogel's Textbook of Practical Organic Chemistry, 4$^{th}$ Ed., Longman, N.Y., 1978, p 426.]

Step 1(c)—Preparation of 2-(2,3-Difluorobenzyl)-2-hexyl-[1,3]dithiolane

Boron trifluoride-acetic acid (9.2 g, 6.8 mmol) was added under an atmosphere of nitrogen to a rapidly stirred mixture of ethane-1,2-dithiol (9.2 g, 8.2 mmol) and the ketone produced in step 1(b) (11.5 g, 48.7 mmol). After stirring at ambient temperature for 2 h water was added and the mixture was extracted with ether (twice). The combined extracts were washed with 2 M aqueous sodium hydroxide, sat. sodium bicarbonate solution and dried. The solvent was removed in vacuo and Kugelrohr distillation (140° C., 0.5 mm Hg) gave the required dithiolane, a pale yellow liquid 4 (14.7 g, 95%); $v_{max}$ 2950, 2920, 2850, 1620, 1590, 1480 s, 1285, 1260, 1220, 1200, 1065, 1005, 990, 830, 785, and 740 cm$^{-1}$, $\delta_H$ 0.89 (3 H, t, Me), 1.24–1.38 (6 H, m, CH$_2$), 1.63 (2 H, m, CH$_2$CH$_2$C), 1.92 (2 H, m, CH$_2$CH$_2$C), 3.02–3.13 (2 H, m, CH$_2$), 3.16–3.25 (2 H, m, CH$_2$),3.26 (2 H, d, J1.5 Hz, CH$_2$Ar), 6.95–7.12 (2-H, m, ArH), and 7.22–7.30 (2 H, m, ArH); m/z 316 (M$^+$), 231, 189 (100%), 170, 153, 139, and 127.

Step 1(d)—Preparation of 1,2-Difluoro-3-(2,2-difluorooctyl)benzene

Hydrogen fluoride-pyridine (70%) (25.2 ml) was added dropwise via a polypropylene syringe fitted with polythene tubing to a rapidly stirred suspension of 1,3-dibromo-5,5-dimethylhydantoin (14.2 g, 49.8 mmol) in dry dichloromethane (150 ml) at −70° C. under dry nitrogen. A solution of the dithiolane of step 1(c) (14.5 g, 45.9 mmol) in dry dichloromethane (150 ml) was added dropwise and the reaction mixture was allowed to slowly warm (cooling bath fitted) to −10° C. The brown homogenous solution was cooled to −70° C. and the mixture was poured quickly into rapidly stirred mixture of basic alumina in dichloromethane cooled with a CO$_2$ (solid)-acetone bath. After warming to ambient the mixture was filtered; the solvent was removed in vacuo and the residue was purified by column chromatography (light petroleum) to give a colourless liquid. Kugelrohr distillation (125° C., 0.1 mm Hg) yielded the pure gem-difluoro compound (6.5 g, 54%); $v_{max}$ 2980, 2965, 2860, 1625, 1595, 1490 s, 1380, 1285, 1270, 1210, 1035, 875, 825, 770, and 740 cm$^{-1}$, $\delta_H$ 0.89 (3 H, t, Me), 1.22–1.39 (6 H, m, CH$_2$), 1.51 (2 H, quint, CH$_2$CH$_2$C), 1.71–1.90 (2 H, m, CH$_2$CH$_2$C), 3.22 (2 H, td, J$_{HF\ vic}$ 16 and J1.5 Hz, CH$_2$Ar), and 6.99–7.15 (3 H, m, ArH); m/z 262 (M$^+$), 187, 176, 172, 165, 151, 141, 135, and 127.

Step 1(e)—Preparation of 2,3-Difluoro-4-(2,2-difluorooctyl)phenylboronic acid 2.5 M n-Butyllithium (8.3 ml, 21 mmol), was added dropwise to a stirred solution of the gem-difluoro compound of step 1(d) (5.41 g, 20.6 mmol) in dry THF (70 ml) at −70° C. under an atmosphere of dry nitrogen at such a rate that the temperature did not rise above −60° C. The temperature was maintained for 2 h and trimethyl borate (4.7 ml, 41 mmol) was added dropwise. The mixture was allowed to warm to ambient temperature overnight and 10% hydrochloric acid was added. After stirring for 15 min the mixture was extracted with ether (twice) and the combined extracts were dried and the solvent was removed in vacuo to give the required boronic acid compound in the form of a creamy solid (5.59 g) which was used without further purification.

Step 1(f)—Preparation of 4'-Bromo-2,3-difluoro-4-(2,2-difluorooctyl)biphenyl

To a degassed mixture of 1-bromo-4-iodobenzene (4.84 g, 17.1 mmol), 1,2-dimethoxyethane (50 ml), and 2 M aqueous sodium carbonate (50 ml) was added tetrakis (triphenylphosphine) palladium (0.593 g, 0.513) mmol) under dry nitrogen. The mixture was heated under gentle reflux with rapid stirring and a solution of the boronic acid compound of step 1(e) (5.24 g, 17.1 mmol) in THF (10 ml) was added dropwise and heated under reflux for 5 h. Water was added and the mixture was extracted with ether (twice) and dried. The solvent was removed in vacuo and the crude product was purified by column chromatography (n-hexane) to give a the required biphenyl compound in the form of a white solid (2.06 g, 29%); $v_{max}$ 2950, 2930, 2870, 2860, 1590 w, 1480, 1465 s, 1390, 1220, 1190, 1130, 1100, 1030, 1010, 895, 840, and 800 cm$^{-1}$, $\delta_H$ (400 MHz) 0.88 (3 H, t, Me), 1.23–1.38 (6 H, m, CH$_2$), 1.53 (2 H, quint, CH$_2$CH$_2$C), 1.78–1.93 (2 H, m, CH$_2$CH$_2$C), 3.24 (2 H, td, J$_{HF\ vic.}$ 16 and J1 Hz, CH$_2$Ar), 7.12 (1 H, t, J8 Hz, 5- or 6-H), 7.14 (1 H, t, J8 Hz, 5- or 6-H), 7.41 (2 H, dd, J8 and 1.5 Hz, 2'- and 6'-H), 7.59 (2 H, d, J8 Hz, 3'- and 5'-H); m/z 418 (M$^+$), 416 (M$^+$), 399, 332, 299, 285 (100%), 283 (100%), 268, 252, 232, and 210.

Step 1(g)—Preparation of 4"-Decyloxy-2,3-difluoro-4-(2,2-difluorooctyl)-1,1':4',1"-terphenyl (Compound 13)

Quantities: bromobiphenyl 7 (0.83 g, 1.94 mmol), 2-(4-decyloxyphenyl)-[1,3,2] dioxaborinane (0.95 g, 2.98 mmol), 1,2-dimethoxyethane (30 ml), 2 M aqueous sodium carbonate (30 ml), tetrakis(triphenyl-phosphine) palladium (67 mg, 0.058 mmol). The experimental procedure was as described for the preparation of the biphenyl compound of step 1(f). The crude product was purified by column chromatography (10% dichloromethane in light petroleum) to give the Compound 13 (0.78 g, 70%) (from ethanol-ethyl acetate); transitions (° C.) C 98.9 SmC 133.5 I; $v_{max}$ 2950, 2920, 2850, 1600, 1500, 1485, 1460 s, 1395, 1285, 1250, 1180, 1130, 1100, 1030, 895, 820, and 800 cm$^{-1}$, $\delta_H$ 0.89 (6 H, overlapping t, 2 x Me), 1.23–1.41 (18 H, m, CH$_2$), 1.23–1.41 (4 H, quint, CH$_2$), 1.75–1.95 (4 H, m, CH$_2$), 3.25 (2 H, br t, CH$_2$Ar), 4.01 (2 H, t, OCH$_2$), 6.99 (2 H, d, J8 Hz, 3"- and 5"-H), 7.14 (1 H, br t, J7 Hz, 5-H), 7.21 (1 H, td, J7 and 1.5 Hz, 6-H), 7.57 (2 H, d, J8 Hz, 2"- and 6"-H), 7.63 (2 H, d, J8 Hz, ArH), and 7.65 (2 H, d, J8 Hz, ArH); m/z 570 (M$^+$), 550, 480, 456, 443, 430 (100%), 413, 401, 387, 372 and 295.

Example 2

In order to reduce the lateral dipole and hence the melting point of the materials, a trifluoro-substituted intermediate 2.5 was prepared starting from compound 2.1 using steps 2(a) to 2(d) in the reaction scheme below in a similar manner to that used in Example 1 to prepare the analogous 1,2-difluorophenyl intermediate. Intermediate 2.5 was then involved in palladium-catalysed cross-coupling reactions with boronic acids 2.6 and 2.8 to generate a monofluorobiphenyl (2.7) and a monofluoroterphenyl (2.9).

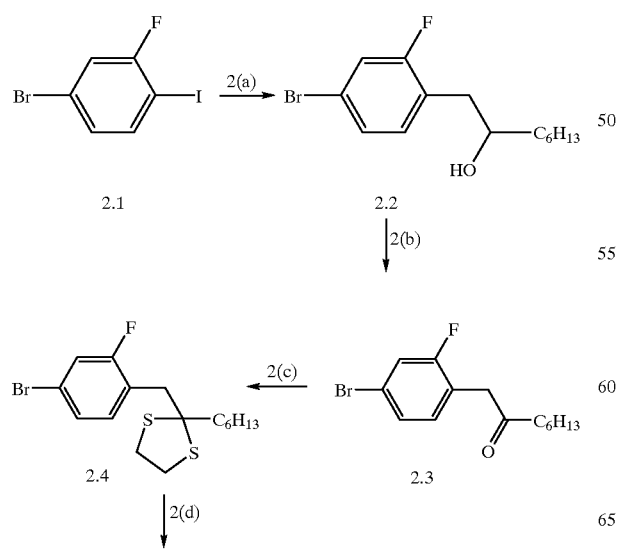

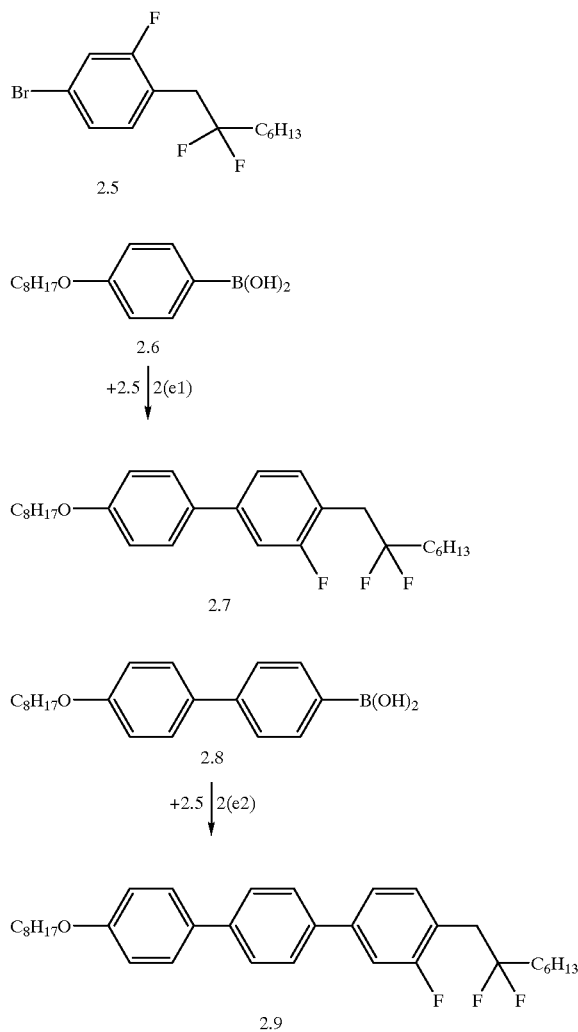

Reagents (a) . . . (i) n-BuLi; (ii) 1,2-epoxyoctane; (iii) BF$_3$.Et$_2$O, −70 to −30° C.

(b) . . . chromic acid, ether (c) . . . ethane-1,2-dithiol, BF$_3$.AcOH (d) . . . HF-pyridine, dibromodimethylhydantoin, CH$_2$Cl$_2$, −70 to −10° C.

(e1/e2) . . . 1,2-dimethoxyethane, Pd(PPh$_3$)$_4$, 2M Na$_2$CO$_3$

Example 3

In order to produce compounds containing the (CH$_2$CF$_2$CH$_2$ CF$_2$R) unit, a novel route (see the reaction scheme below) was devised. The β-diketone (3.6) is considered to be suitable as a intermediate in the synthesis of materials according to the present invention with a tetrafluorinated alkyl chain.

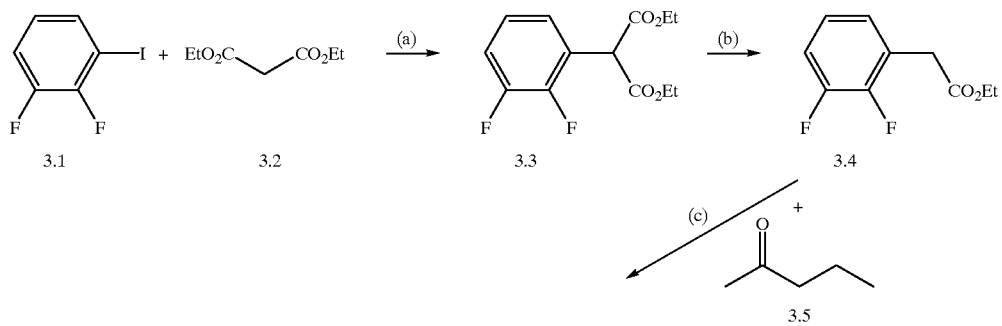
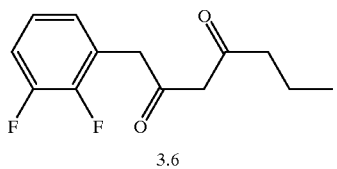
Reagents
- a ... (i) NaH, dioxan; (ii) CuBr
- b ... (i) 2M NaOH, EtOH; (ii) HCl, 80° C.; (iii) EtOH, conc. $H_2SO_4$ reflux
- c ... NaH, THF
Example 4
Compound 4.5 containing a decyloxy chain was prepared according to the reaction scheme below, and compounds 4.6 to 4.10 were prepared by analogous methods.
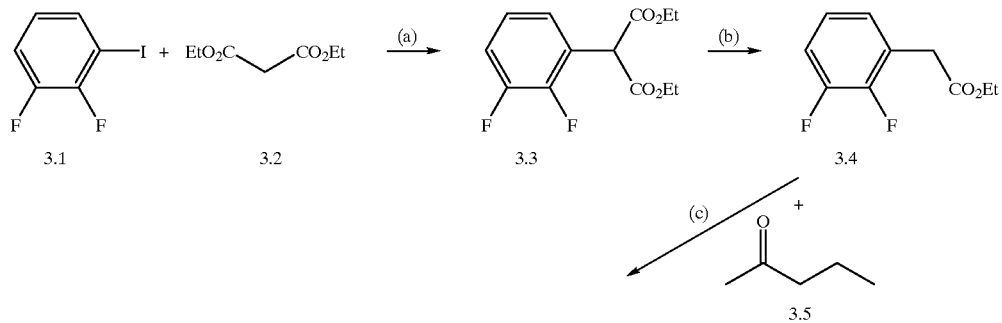
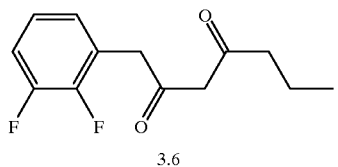
Reagents
- a ... (i) NaH, dioxan; (ii) CuBr
- b ... (i) 2M NaOH, EtOH; (ii) HCl, 80° C.; (iii) EtOH, conc. $H_2SO_4$ reflux
- c ... NaH, THF

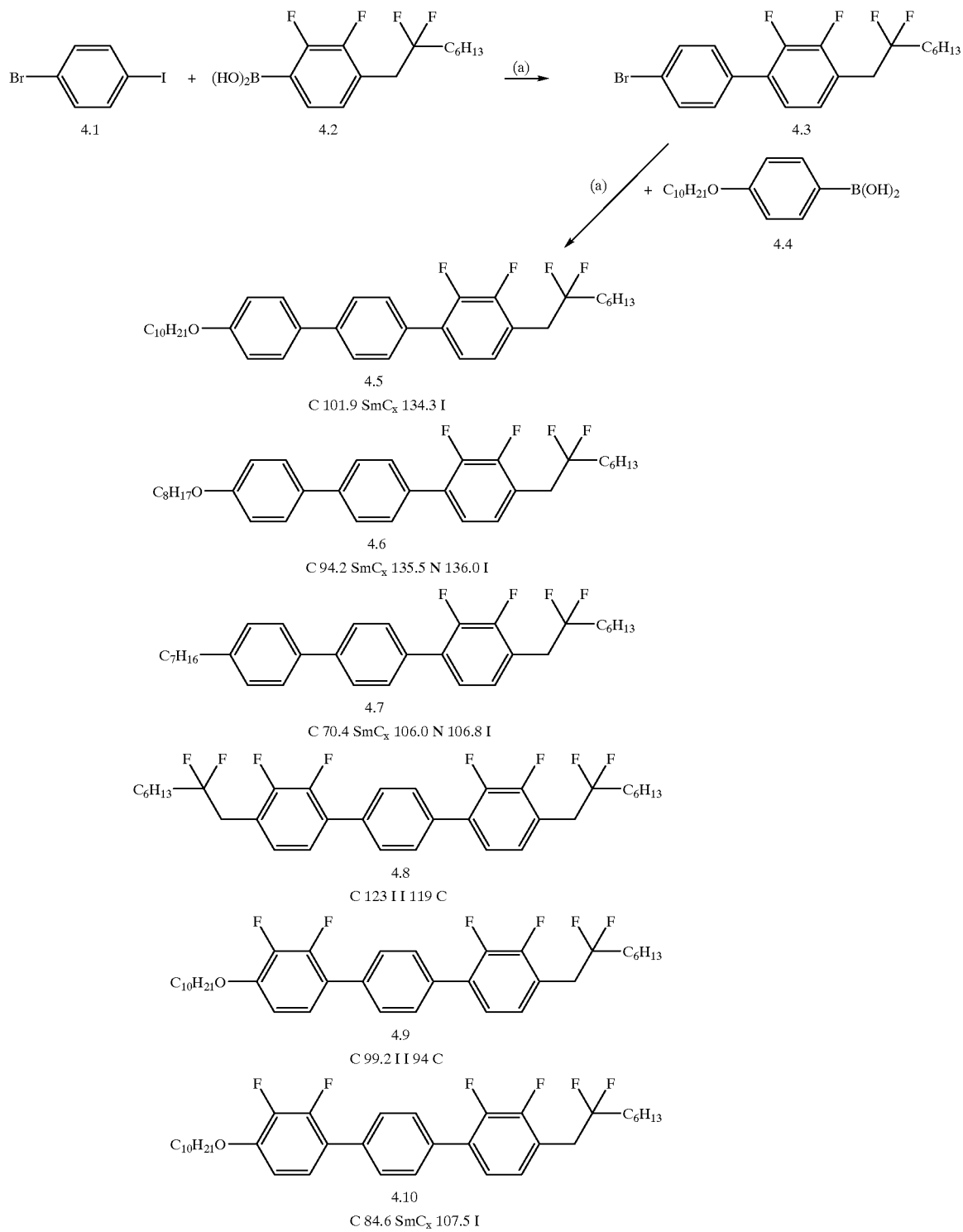

Reagents a . . . 1,2-dimethoxyethane, 2M $Na_2CO_3$, $Pd(PPh_3)_4$

Signs of photo-sensitivity were observed for compound 4.5 with the formation of a greenish colour on the portion of sample exposed to sunlight. Compounds 4.6–4.10 did not exhibit any photo-sensitivity.

Example 5

A similar sequence to that used in Example 4 above was used to prepare the trifluoroterphenyl compound 5.15. The optical microscopy shows a highly birefringent schlieren texture with many multi-brush (six or more) defects. There are also, what appears to be, two brush defects.

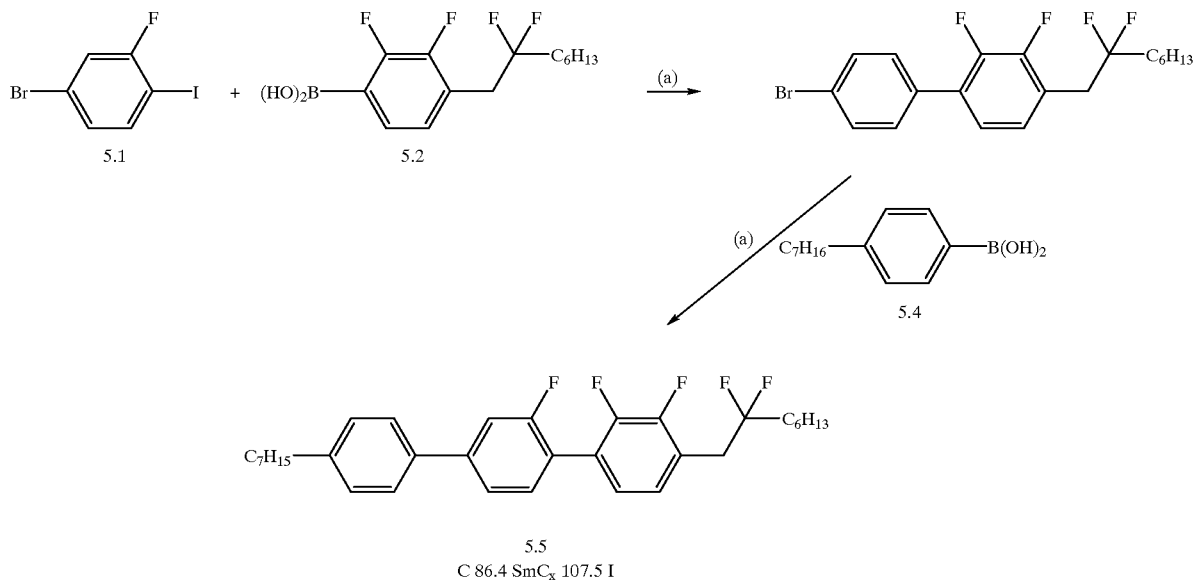

Reagents
  a ... 1,2-dimethoxyethane, 2M Na$_2$CO$_3$, Pd(PPh$_3$)$_4$

Example 6

Dopant for Use in a Liquid Crystal Composition in Conjunction with a Compound According to the Present Invention A β-monofluoroalkyldifluorophenylpyrimidine compound 6.3 was prepared according to the reaction scheme below present invention having a chiral site as a chiral dopant as well as being an additive for enhancing the tranverse dipole moment of a liquid crystal composition.

Example 7

The synthetic scheme below was used to prepare the α,α-difluoro compound 7.9 which exhibits a higher melting point and clearing point than the analogous β-compound There is also a lowering of SmC$_x$ stability and the introduction of a 23° C. SmA phase. The orthogonal phase was never observed for any of the β-fluoro-compounds prepared. The

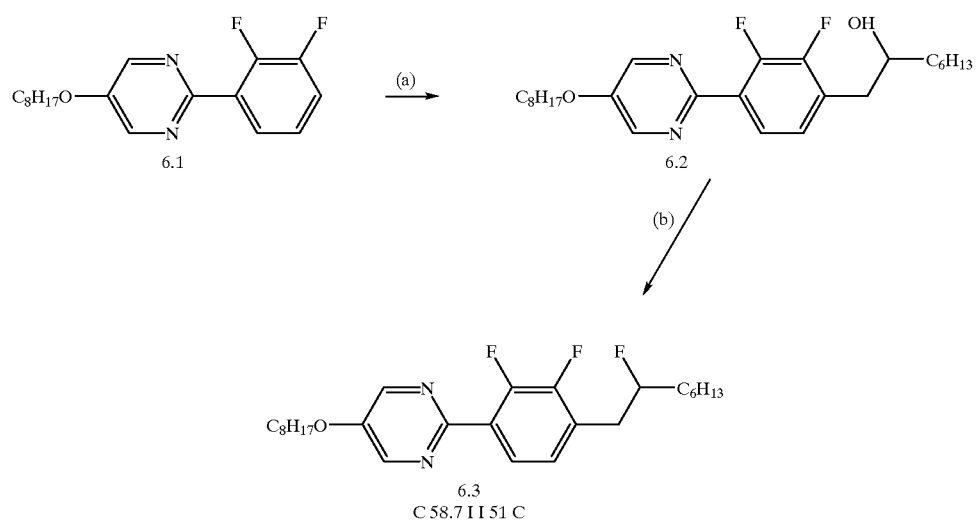

Reagents
  a ... (i) LDA, THF, −90° C.; (ii) 1,2-epoxyoctane; (iii) BF$_3$.Et$_2$O
  b ... DAST. Dichloromethane optical texture is more typical SmC schlieren, but again the two brush defects are quite distinct and indicative of alternating-tilt layers. An alkyl-substituted example 7.10 was also prepared in an analogous way

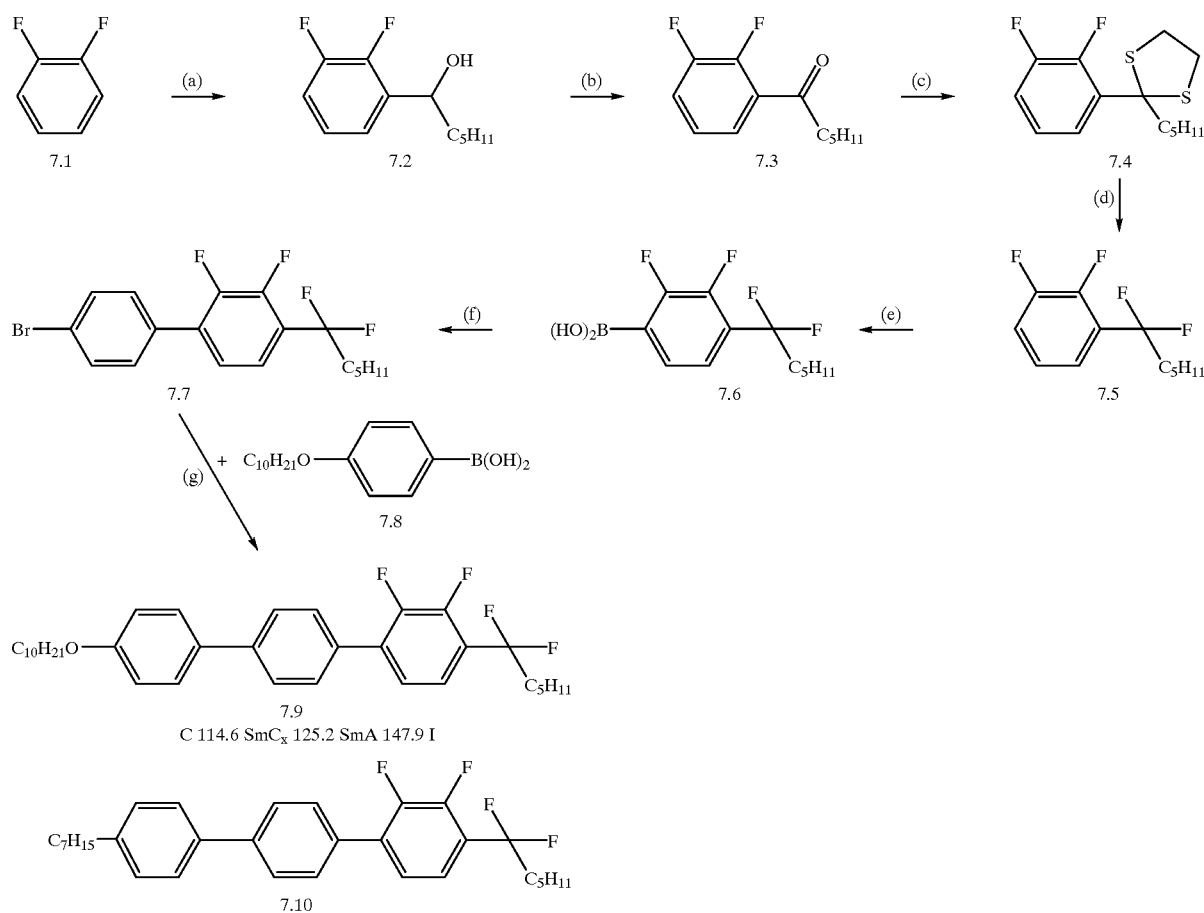
Reagents
a ... (i) n-BuLi; (ii) n-hexanal
b ... chromic acid, ether
c ... 1,2-ethanedithiol, $BF_3.Et_2O$
d ... HF-pyridine, dichloromethane, −70° C.
e ... (i) n-BuLi; (ii) $B(OMe)_3$; (iii) HCl
f ... 1-bromo-4-iodobenzene, 1,2-dimethoxyethane, 2M $Na_2CO_3$, $Pd(PPh_3)_4$
g ... tert-butyl methyl ether, $Pd(PPh_3)_4$, 2M $Na_2CO_3$
Example 8
The reaction scheme below was used to prepare an ether-linked fluorinated chain compound 8.4:
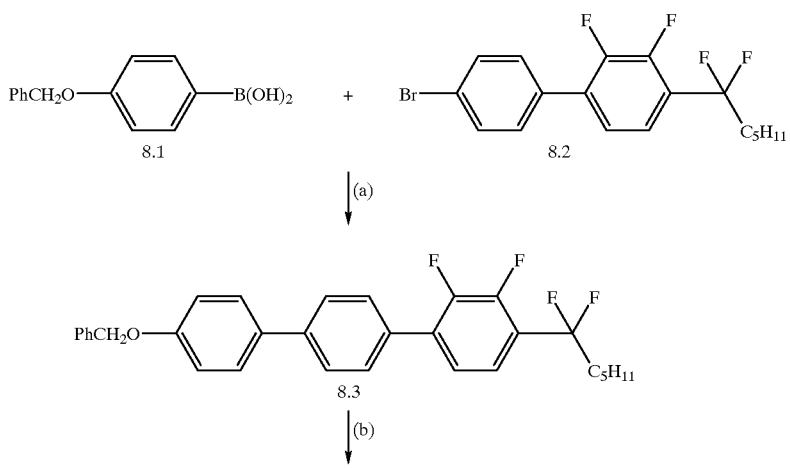

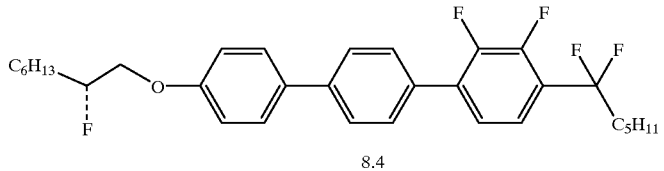

8.4

Reagents a ... tert-butyl methyl ether, Pd(PPh$_3$)$_4$, 2M Na$_2$CO$_3$ b ... (i) Pd/C, ethyl acetate; (ii) (R)-2-fluorooctanol, DEAD, PPh$_3$. THF The improved transverse dipole moments which are achievable by compounds of the present invention will be apparent from the list below:

| Compounds of the Invention | Dipole Moment (×10$^{-30}$ Cm) |
| --- | --- |
| C$_8$H$_{17}$O—[ring]—[ring]—[ring]—CF$_2$—C$_6$H$_{13}$ (trifluoro substituted) | 20.65 |
| C$_8$H$_{17}$O—[ring]—[ring]—C(CF$_3$)—C$_6$H$_{13}$ | 15.81 |
| C$_{10}$H$_{21}$O—[ring]—[ring]—[ring]—C(CF$_3$)—C$_5$H$_{11}$ | 24.52 |
| C$_8$H$_{17}$—[ring]—[ring]—CF$_2$—C$_6$H$_{13}$ | 15.68 |
| C$_{10}$H$_{21}$O—[ring]—[ring]—[ring]—CF$_2$—C$_6$H$_{13}$ | 16.48 |

| Known Compounds | |
| --- | --- |
| C$_7$H$_{15}$—[ring]—[ring]—[ring]—OC$_6$H$_{13}$ (tetrafluoro) | 14.9 |
| C$_6$H$_{13}$O—[ring]—[ring]—[ring]—C$_5$H$_{11}$ (difluoro) | 12.8 |
| C$_6$H$_{13}$O—[ring]—[ring]—[ring]—C$_5$H$_{11}$ (tetrafluoro) | 10.8 |
| C$_9$H$_{19}$O—[ring]—[pyrimidine]—C$_6$H$_{13}$ | 5.2 |

(The dipole moments were measured following the procedure of E. P. Raynes (1984) Mol. Cryst. Liq. Cryst. Lett., v1 p 69)

It has been shown that adding a compound of the invention such as

C$_{10}$H$_{21}$—[ring]—[ring]—[ring]—C(CF$_3$)—C$_5$H$_{11}$

I 143.7 SmA 121.8 SmC 110.5 SmI <25 K Mpt 111.7° C.

C$_{10}$H$_{21}$—[ring]—[ring]—[ring]—C(CF$_3$)—C$_5$H$_{11}$

K 79.6 SmC 84.3 N 95.9 I into a SMC host material, such as that comprising a 1:1:1:1 mixture of compounds H1 to H4 below, retains good phase transitions and that the compound is miscible across the phase diagram:

H1
C$_7$H$_{15}$—[ring]—[ring]—[ring]—C$_5$H$_{11}$

H2
C$_9$H$_{19}$—[ring]—[ring]—[ring]—C$_5$H$_{11}$

-continued

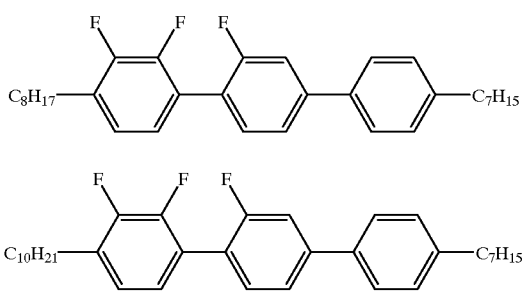

I 119.1–118.8 N 110.7 SmA 99.5 SmC 18.9 K (Mpt=30.2° C.)

The present invention will now be described in further detail and with reference to the accompanying drawing which is a schematic section through an electro-optical liquid crystal device according to the present invention.

BRIEF DESCRIPTION OF DRAWING

FIG. 1/1 is a diagram of a liquid crystal cell.

Referring now to the drawing, the device illustrated therein comprises first and second spaced glass substrates 10 and 12 between which is defined a liquid crystal cell. The mutually facing surfaces of the substrates 10 and 12 are provided with respective rubbed alignment layers 14 and 16 between and in contact with which is disposed a layer 18 of the above-mentioned liquid crystal composition including compound of the formula [13] above.

Linear polarisers 20 and 22 are provided on the outer surfaces of the substrate 10 and the substrate 12, respectively. The polariser 20 has its polarisation axis aligned with the rubbing directions of the alignment layers 14 and 16 which are mutually parallel, whilst the linear polariser 22 has its polarisation axis perpendicular to that of the polariser 20 and the rubbing directions of the alignment layers 14 and 16. The liquid crystal molecules in the chiral smectic phase within the liquid crystal composition in the layer 18 are sensitive to changes in electrical field applied across the layer 18 via the electrodes 24 and 26. Thus, in a manner known per se, the layer 18 can be switched such that light transmission through the device is enabled at one voltage and prevented at another voltage so that the device can act as a fast-operating optical shutter.

The compounds of the present invention are considered to be particularly suitable for the production of liquid crystal compositions used in the following:

(a) Liquid crystal display devices which are to be operated in VAN (vertically aligned nematic) mode where a high negative dielectric anisotropy is required for low voltage switching into the plane of the liquid crystal cell, (b) Ferroelectric crystal devices using AC field stabilisation and/or τ-Vmin (or inverse mode) operation, in which high negative dielectric anisotropy and/or high positive dielectric biaxiality is required.

(c) Highly multiplexed nematic devices which require positive dielectric biaxiality for operation and also a high dielectric constant perpendicular to the long axis of the molecule, for a steep electro-optic response.

(d) Devices where a nematic liquid crystal composition having a large flexoelectric effect is required.

(e) Ferroelectric, antiferroelectric and electroclinic devices generally where a high transverse dipole moment is required.

What is claimed is:

1. A compound of the general formula [2], [3], [4], [5], [6], [7], [8], [9], [10], [11] or [12], wherein R is $(C_1-C_{10})$ alkyl and R' is $(C_1-C_{12})$ alkyl, and v=0 or 1:

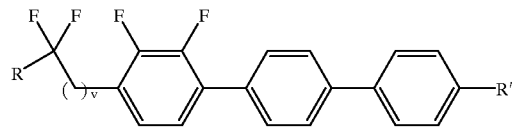

[2]

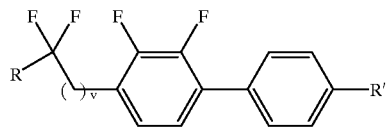

[3]

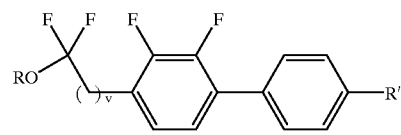

[4]

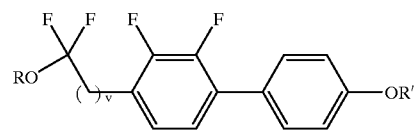

[5]

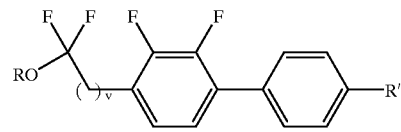

[6]

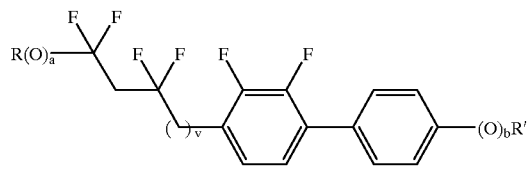

[7]

where a is 0 or 1 and b is 0 or 1

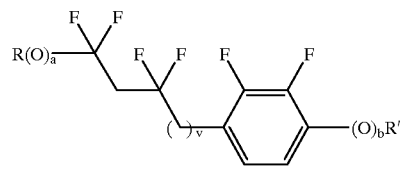

[8]

where a is 0 or 1 and b is 0 or 1

[9]

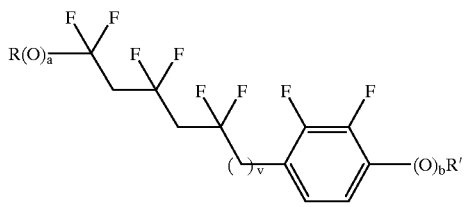

where a is 0 or 1 and b is 0 or 1

[10]

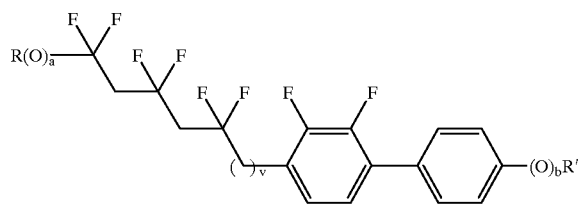

where a is 0 or 1 and b is 0 or 1

[11]

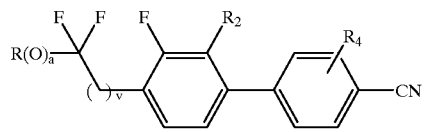

where a is 0 or 1 and $R_2$=H or F and $R_4$=H or F

[12]

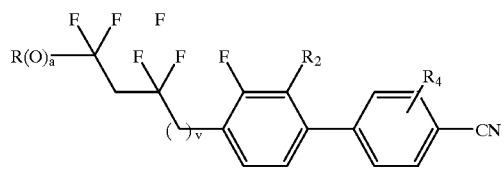

where a is 0 or 1 and $R_2$=H or F and $R_4$=H or F.

2. A compound of the formula [13]:

[13]

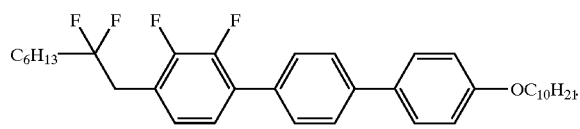

3. A compound of the formula:

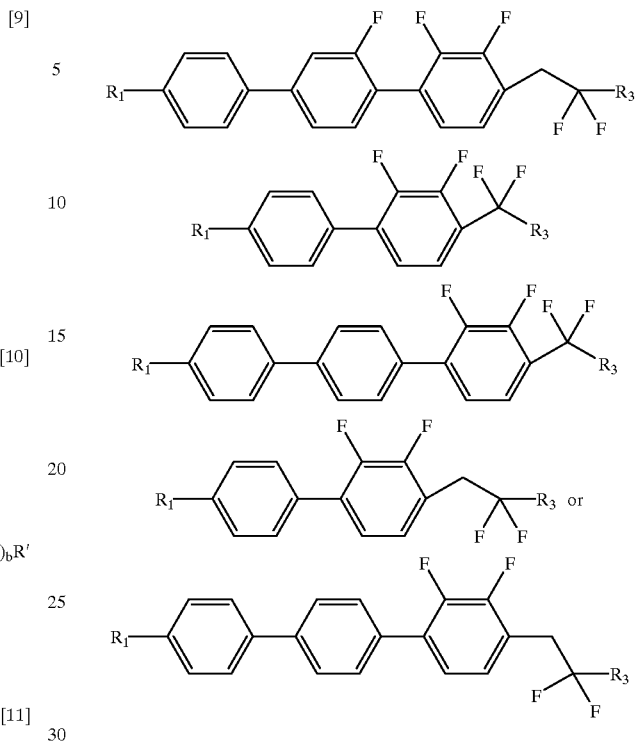

where $R_1$ is $(C_1-C_{12})$alkyl or $(C_1-C_{12})$alkoxy and $R_3$ is $(C_1-C_{12})$alkyl.

4. A liquid crystal composition containing a compound as claimed in claim 1.

5. An electro-optical liquid crystal device including a liquid crystal cell have a layer of a liquid crystal composition as claimed in claim 4, and means for applying an electrical field across said layer.

6. A liquid crystal composition containing a compound as claimed in claim 2.

7. A liquid crystal composition containing a compound as claimed in claim 3.

8. An electro-optical liquid crystal device including a liquid crystal cell having a layer of a liquid-crystal composition as claimed in claim 6, and means for applying an electrical field across said layer.

9. An electro-optical liquid crystal device including a liquid crystal cell having a layer of a liquid crystal composition as claimed in claim 7, and means for applying an electrical field across said layer.

* * * * *